United States Patent
Beghuin et al.

(10) Patent No.: US 8,422,822 B2
(45) Date of Patent: Apr. 16, 2013

(54) FOURIER TRANSFORM DEFLECTOMETRY SYSTEM AND METHOD

(75) Inventors: Didier Beghuin, Enghien (BE); Luc Joannes, Gembloux (BE)

(73) Assignee: Lambda-X, Nivelles (BE)

( * ) Notice: Subject to any disclaimer, the term of this patent is extended or adjusted under 35 U.S.C. 154(b) by 382 days.

(21) Appl. No.: 12/743,539

(22) PCT Filed: Nov. 6, 2008

(86) PCT No.: PCT/EP2008/065082
§ 371 (c)(1),
(2), (4) Date: Jul. 23, 2010

(87) PCT Pub. No.: WO2009/065740
PCT Pub. Date: May 28, 2009

(65) Prior Publication Data
US 2010/0310130 A1   Dec. 9, 2010

(30) Foreign Application Priority Data
Nov. 19, 2007  (EP) .................................. 07121009

(51) Int. Cl.
*G06K 9/36*  (2006.01)

(52) U.S. Cl.
USPC ............................................................. 382/280

(58) Field of Classification Search ............. 382/280
See application file for complete search history.

(56) References Cited

U.S. PATENT DOCUMENTS 4,790,550 A * 12/1988 Simpson .................. 280/87.042
4,791,584 A * 12/1988 Greivenkamp, Jr. .......... 356/513

(Continued)

FOREIGN PATENT DOCUMENTS

WO     2004/025568 A2   3/2004
WO     WO 2004025568 A2 *   3/2004

OTHER PUBLICATIONS

Fourier transform—interferometry, Takeda et al., XP000570893, 1983, pp. 156-160.*

(Continued)

*Primary Examiner* — Jayesh A Patel
(74) *Attorney, Agent, or Firm* — Sughrue Mion, PLLC

(57) ABSTRACT

The present invention relates to a Fourier transform deflectometry system (1) and method for the optical inspection of a phase and amplitude object (2) placed in an optical path between a grating (3) and an imaging system (4), at a distance h of said grating 3. The grating (3) forms a contrast-based periodic pattern with spatial frequencies $\mu_0$, $v_0$ in, respectively, orthogonal axes x,y in an image plane, and the imaging system (4) comprises an objective (5) and an imaging sensor (6) comprising a plurality of photosensitive elements. Spatial frequencies $\mu_0$, $v_0$ are equal or lower than the Nyquist frequencies of the imaging system in the respective x and y axes. According to the method of the invention, a first image of said pattern, distorted by the phase and amplitude object (2), is first captured through the objective (5) by the imaging sensor (6). Then, a Fourier transform of said first image in a spatial frequency domain is calculated, at least one first- or higher-order spectrum of said Fourier transform is selected and shifted in said frequency domain, so as to substantially place it at a central frequency of said Fourier transform, and a reverse Fourier transform said at least one shifted first- or higher-order spectrum of said Fourier transform is performed so as to obtain a complex function $g(x,y)=l(x,y)e^{i\phi(x,y)}$, wherein $l(x,y)$ is an intensity and $\phi(x,y)$ a phase linked to optical deflection angles $\theta_x$, $\theta_y$ in, respectively, the directions of the x and y axes, in the following form: $\phi(x,y)=-2\pi h(\mu_0 \tan\theta_x + v_0 \tan\theta y)$.

22 Claims, 11 Drawing Sheets

U.S. PATENT DOCUMENTS

| | | | |
|---|---|---|---|
| 4,794,550 A | 12/1988 | Greivenkamp, Jr. | |
| 6,100,990 A | 8/2000 | Ladewski | |
| 6,130,419 A * | 10/2000 | Neal | 250/201.9 |
| 6,496,253 B1 * | 12/2002 | Vokhmin | 356/124 |
| 6,717,661 B1 * | 4/2004 | Bernstein et al. | 356/121 |
| 6,771,362 B2 * | 8/2004 | Keren et al. | 356/124 |
| 2004/0189938 A1 * | 9/2004 | Eagan | 351/208 |
| 2005/0276513 A1 * | 12/2005 | Ojanen et al. | 382/286 |
| 2007/0229848 A1 * | 10/2007 | Yamamoto | 356/515 |

OTHER PUBLICATIONS

European Office Action for Appln. No. 08 852 427.7-2204, dated Apr. 26, 2011.

Multi-frequency and multiple phase-shift sinusoidal fringe projection for 3D profilometry; E. B. Li; Received Dec. 16, 2004; Mar. 7, 2005/ vol. 13, No. 5; Optics Express 1561.

Fringe-pattern analysis using a 2-D Fourier transform; Bone, et al.; May 15, 1986; vol. 25, No. 10/ Applied Optics; 1653-1660.

Fourier transform profilometry based on a fringe pattern with two frequency components; Wenjing Chen, et al; Science Direct; Mar. 13, 2006; www.sciencedirect.com.

Two-dimensional fringe-pattern analysis; William W. Macy, Jr., ; Applied Optics; 2219; vol. 22 Dec. 1983, No. 23, New York.

Fourier-transform method of fringe-pattern analysis for computer-based topography and interferometry; J. Opt. Soc. Am/ vol. 72, No. 1/ Jan. 1982; Mitsuo Takeda, et al.

* cited by examiner

FOURIER TRANSFORM DEFLECTOMETRY SYSTEM AND METHOD

The present invention relates to a deflectometry system and method for the optical inspection of a phase and amplitude object.

When a refractive object is illuminated, the traversing wavefront is affected according to the shape and refractive index of the object. The intensity of the light will also be affected by the transmission of the object. Likewise, when light is reflected on a reflective object, the shape of the reflecting surface of the object will affect the reflected wavefront and its reflectivity the intensity of the reflected light. The optical characteristics of the refractive or reflective object can thus be determined.

In the optical industry, it is crucial for inspectors to be able to determine the optical characteristics of products in as precise, complete and automated manner as possible. In particular, as tailored corrective spectacle or contact lenses with complex curvatures are developed, it is very important to be able to control that each lens conforms to its particular specification.

Similar inspection methods are also used in other fields, such as for the inspection of semiconductor wafers, flat glass panels, plastic sheets, etc. where the shape and/or surface finish of optically reflective and/or refractive objects needs to be inspected in a precise and efficient manner.

Several systems and methods for the optical characterisation of refractive and/or reflective objects have been previously disclosed. They can be categorised, i.a. by whether they extract information regarding the wavefront, its first order derivative, i.e. its inclination, or its second order derivative, i.e. its curvature.

The systems and methods belonging to the first category comprise direct interferometry, as carried out with Michelson, Mach-Zendher, or Fizeau interferometers, or with any other type of interferometers wherein the wavefront to be analyzed interferes with a non aberrated reference wavefront, which can be spherical, plane, or aspherical. A deep review of such systems and methods was disclosed in Daniel Malacara, <<Optical Shop Testing>>, $2^{nd}$ edition, John Wiley & Sons, Inc., New York, 1992, ISBN 0-471-52232-5.

Another technique in this category is digital holography, as disclosed in International Patent Application WO 00/20929.

The main drawbacks of these systems and methods of the first category is that they require coherent light, which is subject to optical noise capture, as well as a reference wavefront, and that they are quite limited in dynamic range.

The most numerous existing optical characterisation systems and methods are probably those belonging to the second category. This category comprises, i.a. the Hartmann test, Foucault test, Ronchi test, Differential Interference Contrast microscopy (DIC), Shearing interferometry, lateral shift interferometry, Talbot moiré, Shack-Hartmann tests, deflectometry, moiré deflectometry, phase-shift Schlieren, and scanning deflectometry. Some of them are also described in the above mentioned book, <<Optical Shop Testing>>.

Compared to those of the first category, these techniques present the advantages of accepting larger wavefront deformations, i.e. a larger dynamic range, and not requiring a reference wavefront. However, this extent of dynamic range is often at the cost of sensitivity. An additional drawback of these techniques is that recovering the wavefront requires the integration of the derivative signal obtained by these methods. This is discussed, for instance in C. Elster, I. Weingärtner, "Solution to the shearing problem", Appl. Opt., 38 (1999) 5024-5031.

Some of the disclosed techniques allow the simultaneous acquisition of the derivatives of the wavefront in two axes, e.g. the shear interferometry system and method using a grating with two orthogonal directions disclosed in J. C. Wyant, "Double Frequency Grating Lateral Shear Interferometer", App. Opt., 12(9), p. 2057-2060, 1973; the lateral shift interferometry system and method disclosed in J. Primot, S. Velghe, N. Gérineau, R. Haïdar, J-C. Chanteloup, << L'analyse de surface d'onde par interférométrie à décalage multilatéral>>, Photoniques, 19, p. 57, 2005; the adapted two-directional Shack Hartmann and Ronchi tests disclosed, respectively in Xavier Levecq, Samuel Bucourt, "Analyseur de font d'onde: les évolutions des analyseurs Shack-Hartmann>>, photoniques", 19, p. 53, 2005; and A. Cordero-Davila, E. Luna-Aguilar, S. Vazquez-Montiel, S. Zarate-Vazquez, and M. E. Percino-Zacarias, "Ronchi test with a square grid", App. Opt. 37(4), p. 672-675, 1998; or the moiré deflectometry systems and methods disclosed in, e.g. Jesus Villa, Juan Antonio Quiroga, and Manuel Servin, "Improved regularized phase-tracking technique for the processing of squared-grating deflectograms", App. Opt. 39 (4), p. 502-508, 2000, or U.S. Pat. No. 6,771,362.

Those wavefront differential-based techniques do nevertheless present the drawback of a limited spatial resolution. The spatial resolution is limited, for instance, by the lateral shear in shear interferometry systems; by the discretization due to finite number of micro-lenses in the Shack Hartmann test, as disclosed in U.S. Pat. No. 6,130,419; or by the separation of the features of the pattern used in the deflectometry method described in U.S. Pat. No. 6,496,253. As a result, the wavefront can only be reconstructed with a limited spatial resolution. The high spatial frequencies are then not accessible to those methods, which makes them inadequate, for instance, for the detection of small defects such as scratches, dust, tooling marks or pitting, as well as that of micro-engravings as used in progressive ophthalmic lenses for spectacles. Other inspection means, such as, e.g. dark field lighting, are thus necessary for these purposes. The specification of International Patent Application WO 2005/121740 A1 summarizes well this problem, and proposes a solution based on the use of alternating patterns.

The same problem also occurs in moiré deflectometry and Talbot interferometry, as disclosed in Juan Antonio Quiroga, Daniel Crespo, Eusebio Bernabeu, "Fourier transform method for automatic processing of moiré deflectograms", Opt. Eng. 38 (6), p. 974-982, 1999, and in the abovementioned Villa et al. article. In the deflectometry method disclosed in U.S. Pat. No. 6,771,362, the problem of spatial resolution is tackled by increasing the axial separation between 2 square grids, but this remains limited to relatively low spatial resolutions. Similar arrangements have been disclosed in US2004/189938 and U.S. Pat. No. 6,717,661.

A phase-shifting Schlieren method has proven suitable for accurately obtaining not only quantitative information regarding wavefront curvature e.g. to be fitted by Zernike polynomials, but also high spatial resolution content information regarding phase or absorption, as disclosed in L. Joannes, F. Dubois, J-C. Legros, "Phase-shifting Schlieren: high-resolution quantitative Schlieren that uses the phase-shifting technique principle", App. Opt. 42(25), p. 5046-5053, 2003; and in International Patent Application WO 03/048837. This is made possible by the coding of both the phase and intensity for every pixel of the image captured by an imaging sensor. However, this phase-shifting Schlieren method has the disadvantage of requiring comparatively complicated and costly equipment.

The third category of optical characterisation systems and methods, those obtaining the second-order derivative or curvature of the wavefront comprise i.a. the Makyoh mirror test based technique, as disclosed, for instance in Ferenc Riesz, I. E. Lukas, and J. P. Makai, "Realisation of quantitative Makyoh topography using a Digital Micromirror Device", Optical Measurement System for Industrial Inspection, V, Wolfgang Osten, Christophe Gorecki, Erik L. Novak, proc SPIE 6616, 66160L (2007). In this method, the curvature of the wavefront curvature directly leads to an intensity modification in relation to the propagation length. This intensity variation is recorded and analyzed. Note that the raw information obtained by the systems and methods of the second category, that is, information related to the first-order derivative of the wavefront, in some cases can be processed so as to obtain the wavefront curvature, as disclosed, for instance, in Hector Canabal, J. Antonio Quiroga, and Eusebio Bernabeu, "Automatic processing in moiré deflectomertry by local fringe direction calculation", App. Opt. 37(25), p. 5894-5901, 1998.

A numerical method to analyze dense fringe patterns in interferometry or profilometry was disclosed in Mitsuo Takeda and Kazuhiro Muthoh, "Fourier transform profilometry for the automatic measurement of 3-D object shapes", App. Opt. 22(24), p. 3977-3982, 1983; and Mitsuo Takeda and Seiji Kobayashi, "Lateral aberration measurements with a digital Talbot interferometer", App. Opt. 23 (11), p. 1760-1764, 1984. According to this method, a numerical Fourier transform of the fringe pattern image signal is filtered and shifted in the Fourier domain. The inverse Fourier transform of the filtered and shifted Fourier transform is then calculated, and its phase map retrieved. This method is referred to as Fourier Method. This numerical method can be seen as the computational form of holography and led to digital holography, as disclosed in patent WO 00/20929. It was shown, for instance in D. Beghuin, E. Cuche, P. Dahlgren, C. Depeursinge, G. Delacrétaz, and R. P. Salathé, "Single acquisition polarisation imaging with digital holography", Electronics Letters 35: 2053-2055 (1999), that the numerical Fourier Method can be used for processing multiple zones in the Fourier domain. For the numerical Fourier Method to work correctly, the spatial content of the phase should not be large compared to the carrier frequency (see M. Takeda, H. Ina, and S. Kobayashi, "Fourier-transform method of fringe-pattern analysis for computer-based topography and interferometry", J. Opt. Soc. Am. 72, 156 (1982)). In off-axis holography, for instance, the reference wavefront shall thus be at quite a large angle to the object wavefront. In other words, in order to get a sufficiently large dynamic range, the carrier frequency shall be as high as possible, which in practice is limited by the definition of image sensors. In the article Jonas Kuhn, Tristan Colomb, Frederic Monfort, Florian Charrière, Christian Depeursinge, "Real-time dual-wavelength digital holographic microscopy with a single hologram", proc SPIE vol 6616, it has been disclosed that two frequency carriers sufficiently far apart in the Fourier domain can serve for unambiguous phase unwrapping if the two signals carry the same information, i.e. in this case optical distances.

Turning back to the abovementioned U.S. Pat. No. 6,496, 253 B1, that document disclosed a deflectometry method for the optical inspection of a phase and amplitude object placed in an optical path between a single grating and an imaging system. The grating forms a contrast-based periodic pattern, and the imaging system comprises an objective and an imaging sensor comprising a plurality of sensor elements. Performing this method comprises the step of capturing through the objective, with the imaging sensor, an initial image of said pattern distorted by the phase and amplitude object.

However, as stated above, this method had the significant drawback of a limited spatial resolution. High spatial frequency patterns are not accessible for this method and small features and defects in the object thus cannot be revealed by this method.

In order to solve this problem, the method of the invention further comprises, in addition to the abovementioned features of the deflectometry method of U.S. Pat. No. 6,496,253, the steps of:

calculating a Fourier transform of said initial image in a spatial frequency domain;

selecting at least one first- or higher-order spectrum of said Fourier transform and shifting it in said frequency domain, so as to substantially place it at a central frequency of said Fourier transform; and carrying out a reverse Fourier transform of said at least one shifted first- or higher-order spectrum of said Fourier transform so as to obtain a complex function $g(x,y)=I(x,y)e^{i\phi(x,y)}$, wherein $I(x,y)$ is an intensity and $\phi(x,y)$ a phase, and said phase $\phi(x,y)$ is linked to optical deflection angles $\theta_x$, $\theta_y$ in, respectively, the directions of the x and y axes, according to the following formula: $\phi(x,y)=-2\pi h(\mu_0 \tan\theta_x + v_0 \tan\theta_y)$. h is the distance between the grating and the phase and amplitude object, x and y are orthogonal axes in an image plane, and $\mu_0$ and $v_0$ are, respectively, spatial frequencies of the periodic pattern in the x and y axes, equal or lower than the Nyquist frequencies of the imaging system in the respective x and y axes.

By "Nyquist frequency" it is meant a frequency corresponding to half the sampling frequency of a discrete signal processing system. According to the Nyquist-Shannon sampling theorem, signal aliasing can be avoided if the Nyquist frequency is higher than the maximum frequency of the signal being sampled. The spatial sampling frequency in a given direction of an imaging sensor comprising a plurality of photosensitive elements is the inverse of the distance between adjacent photosensitive elements in that direction. The Nyquist frequency of the imaging system in a given direction corresponds to the Nyquist frequency of the imaging sensor in that direction, multiplied by the magnification factor of the objective. With spatial frequencies $\mu_0$, $v_0$ not higher than the corresponding Nyquist frequencies of the imaging sensor, the distorted pattern image is to be fully resolved, preventing thus the formation of moiré fringes. By contrast, the moiré contouring method described in the prior art document U.S. Pat. No. 4,794,550 generates moiré fringes through image aliasing by using patterns with spatial frequencies higher than the Nyquist frequencies of an imaging system.

If the grating forms, for example, a high spatial frequency sinusoidal pattern of parallel straight fringes, the undistorted image of the grating on the imaging sensor could be described by the following function $f$ of the image coordinates x,y:

$$f(x,y)=I_0(1+V_0\cos(2\pi\mu_0 x+2\pi v_0 y+\Phi)) \quad (1)$$

where $V_0$ is the visibility of the undistorted fringe pattern at the imaging sensor, $\Phi$ is a constant phase, and $I_0$ the average brightness.

When the phase and amplitude object is inserted between the grating and the imaging system, it distorts the image of the grating on the imaging sensor.

Once distorted, the image f(x,y) can thus be expressed as:

$$f(x,y)=I_0 T(x,y)(1+V(x,y)\cos(2\pi\mu_0 x+2\pi v_0 y+\Phi+\phi(x,y))) \quad (2)$$

where $T(x,y)$ is the local transmission of the object, which is assumed to vary slowly, $V(x,y)$ is the local visibility of the distorted fringe pattern, which reflects high-spatial frequency features of the object, and φ(x,y) is the local phase.

The equation (2) of the distorted image has two terms, $f_1(x,y)$ and $f_2(x,y)$, wherein the first term $f_1(x,y)$ equals $I_0T(x,y)$, that is, the transmission intensity of the object, whose Fourier transform will be centred onto the central frequency in the frequency domain (Fourier domain). Assuming that the constant phase $\Phi=0$, the second term $f_2(x,y)$ can be expressed as follows:

$$f_2(x,y) = I(x,y)(e^{i(2\pi\mu_0 x + 2\pi v_0 y + \phi(x,y))} + e^{-i(2\pi\mu_0 x + 2\pi v_0 y + \phi(x,y))}) \quad (3)$$

wherein I(x,y) is real, and equals half the product of the transmission intensity $I_0T(x,y)$ of the object (or its reflection intensity, in the case of a reflective object) by the local visibility of the patterns V(x,y).

Since $f_2(x,y)$ is itself the sum of two terms that are identical except in the sign of their phase, each first-order spectrum of the Fourier transform of the image f(x,y) will correspond to the Fourier transform of one of these terms. Designating the Fourier transform of the first one of these two terms as F(µ,v), where µ and v are the frequency coordinates:

$$F(\mu, v) = \int_{-\infty}^{\infty}\int I(x,y)(e^{i(2\pi((\mu_0-\mu)x+(v_0-v)y)+\varphi(x,y))})dx\,dy \quad (4)$$

In the frequency domain, said first-order spectrum is thus offset by approximately $(\mu_0, v_0)$ from the central frequency of the Fourier transform. Shifting F(µ,v) towards the centre of the frequency domain by a coordinate change to the coordinates (µ',v'), wherein, for example, $\mu'=\mu-\mu_0$ and $v'=v-v_0$, results in F(µ',v'):

$$F(\mu', v') = \int_{-\infty}^{\infty}\int I(x,y)(e^{-i2\pi(\mu' x + v' y) + i\varphi(x,y)})dx\,dy \quad (5)$$

F(µ',v') is the Fourier transform of the above-mentioned complex function g(x, y). Thus, carrying out the reverse Fourier transform of F(µ',v') will lead us to that function, and, therefore, to the phase and intensity functions.

The local phase φ(x,y) is related to the first-order derivatives of the wavefront W(x,y). If the angular deviations of a light ray in, respectively, the x and y directions are denominated $\theta_x$ and $\theta_y$, the tangents of these angular deviations will be expressed as follows:

$$\tan(\theta_x) = \frac{\partial W(x,y)}{\partial x}, \quad \tan(\theta_y) = \frac{\partial W(x,y)}{\partial y} \quad (7)$$

The phase φ(x,y) is linked to these angular deviations $\theta_x$ and $\theta_y$, namely in the following form:

$$\phi(x,y) = -2\pi \tan(\theta_x)h\mu_0 - 2\pi \tan(\theta_y)hv_0 \quad (8)$$

where h is the distance between the grating and the wavefront, and where it is considered that a positive power phase object results in positive angular deviations $\theta_x$ and $\theta_y$.

Although the Fourier method applied in the invention is similar to that applied in the abovementioned Fourier transform profilometry method, in those prior art disclosures this was used in conjunction with a different optical setup using a focussed projector. As a result, the resulting phase was directly linked to the profile of the inspected object, instead of to the first-order derivatives of the wavefront, as in the present invention. This made them less suitable for the optical applications of the present invention. Moreover, besides of the first-order derivatives of the wavefront, the method of the invention can also be used to detect high spatial frequency features of the object, such as small defects and micro-engravings. As seen above, the complex function g(x,y) has an amplitude I(x,y). Since $I(x,y)=I_0T(x,y)V(x,y)/2$, such features affecting the local transmission, reflectivity or fringe pattern visibility of the object will be revealed by this amplitude I(x,y).

In US 2007/0229848 a similar Fourier method is also applied. However, it is applied, not on a fully resolved, distorted image of a grating pattern, but on an interference pattern. It is thus not a deflectometry method in the sense of the present invention, and does not have the same results or applications.

The method of the invention can thus provide both a general wavefront shape and small local transmission or reflectivity features, and this with a comparatively simple optical setup.

Advantageously, several first- and/or higher order spectra of said Fourier transform are selected and shifted in said frequency domain so as to substantially place them at a central frequency of said Fourier transform. This has the advantage of improving the signal/noise ratio of the deflectometry method of the invention.

Advantageously, the method of the invention may further comprise a step of unwrapping said phase, thus permitting the retrieval of a continuous wavefront shape. How to perform such a phase unwrapping step is well-known to the skilled person, for instance from Dennis C Ghiglia, Mark D. Pritt, "Two-dimensional phase unwrapping, Theory, Algorithms and Software", John Wiley & Sons, Inc, New York, 1998, ISBN 0-471-24935-1.

Advantageously, the method of the invention may further comprise a step of filtering out said intensity below a certain threshold. By thresholding the intensity, it is possible to obtain a high contrast intensity map allowing clear recognition of small features in the object.

Advantageously, said steps may be carried out with two patterns aligned at an angle with respect to each other. The two patterns can be used subsequently or simultaneously in the form of e.g. a composition of two Ronchi patterns superimposed on the same glass plate. By processing the distorted images of two different, non-parallel patterns by the above-mentioned Fourier method, two local phases $\phi_A(x,y)$ and $\phi_B(x,y)$ are obtained. The local first-order derivatives can then be retrieved from the following two-equation system:

$$\varphi_A(x,y) = -2\pi\frac{\partial W(x,y)}{\partial x}h\mu_{0,A} - 2\pi\frac{\partial W(x,y)}{\partial y}hv_{0,A} \quad (9)$$

$$\varphi_B(x,y) = -2\pi\frac{\partial W(x,y)}{\partial x}h\mu_{0,B} - 2\pi\frac{\partial W(x,y)}{\partial y}hv_{0,B} \quad (10)$$

where $\mu_{0,A}$ and $v_{0,A}$ are the spatial frequencies of the first pattern in the x and y directions and $\mu_{0,B}$ and $v_{0,B}$ are the spatial frequencies of the second pattern in the x and y directions.

Advantageously, said steps may be carried out with the grating in a first position with respect to the object and with the grating in a second position with respect to the object, said first and second positions being offset by a known distance along the optical path. Since the equations are linear, it is possible to calculate the difference between the phases retrieved from the images of the same pattern distorted by the same object at these two different positions separated by said known distance $\Delta h$ along the optical axis. This phase difference $\Delta\phi(x,y)$ can also be expressed as:

$$\Delta\phi(x,y) = -2\pi \tan(\theta_x)\Delta h\mu_0 - 2\pi \tan(\theta_y)\Delta h\nu_0 \qquad (11)$$

Thus, using the same abovementioned two different, non-parallel patterns, it is also possible to obtain a two-equation system as follows:

$$\Delta\varphi_A(x, y) = -2\pi \frac{\partial W(x, y)}{\partial x}\Delta h\mu_{0,A} - 2\pi \frac{\partial W(x, y)}{\partial y}\Delta h\nu_{0,A} \qquad (12)$$

$$\Delta\varphi_B(x, y) = -2\pi \frac{\partial W(x, y)}{\partial x}\Delta h\mu_{0,B} - 2\pi \frac{\partial W(x, y)}{\partial y}\Delta h\nu_{0,B} \qquad (13)$$

So, even if the precise distance between the grating and the object in either position are unknown, with a known distance difference $\Delta h$ it is still possible to retrieve the first-order derivatives of the wavefront in the x and y axes.

In either case, the wavefront can then be integrated from its first-order derivatives in the x and y axes by any numerical integration method known to the skilled person. Examples of such numerical integration methods can be found in L. P. Yaroslaysky, A. Moreno. and J. Campos, "Numerical Integration of Sampled Data for Shape Measurements: Metrological Specifications", p. 380-387, in W. Osten, "Fringe 2005", Springer-Verlag, Berlin, 2006. A Zernike polynomial fitting of the wavefront based on the first order derivatives can also be found in Hedser van Brug, "Zernike polynomials as a basis for wave-front fitting in lateral shearing interferometry", A.O., 36-13, p. 2788-2790, 1997.

Advantageously, in the method of the invention, several distorted images of the pattern may be captured, with the object at several distances in said optical path with respect to the grating, and the method may additionally comprise the steps of:
  combining said multiple distorted images of the pattern to obtain a composite image;
  calculating a Fourier transform of said composite image in a spatial frequency domain;
  selecting at least one first- or higher-order spectrum of said Fourier transform of the composite image and shifting it in said frequency domain so as to substantially place it at a central frequency of said Fourier transform; and
  carrying out a reverse Fourier transform of said at least one shifted first- or higher-order spectrum of said Fourier transform of the composite image so as to obtain a complex function $g_M(x,y) = I_M(x,y)e^{i\phi_M(x,y)}$ wherein $I_M(x,y)$ is an intensity and $\phi_M(x,y)$ a phase, and $I_M(x,y)$ is linked to the contrast level in the composite image.

The analysis of the composite image using the abovementioned Fourier method can be used to locate the optical centre of the object. A map of the amplitude $I_M(x,y)$ of the output of applying this Fourier method to such a composite image will show fringes corresponding to areas of least or most contrast, at least one of which contains an optical centre of the object.

Said combination could be carried out by for instance digital addition, subtraction or multiplication of the distorted pattern images.

Even more advantageously, said pattern may comprise two crossed sets of parallel fringes, and said steps of calculating a Fourier transform of the composite image, selecting and shifting said spectrum of said Fourier transform of the composite image, and carrying out a reverse Fourier transform of said shifted spectrum of the Fourier transform of the composite image may be carried out first with a shift close to $\mu_{0,A}$, $\nu_{0,A}$, and then with a shift close to $\mu_{0,B}$, $\nu_{0,B}$ so as to obtain two amplitude maps, respectively $I_{MA}(x,y)$ and $I_{MB}(x,y)$, so as to obtain two amplitude maps $I_{MA}(x,y)$ and $I_{MB}(x,y)$. The two patterns can be in the same grating, e.g. as a composition of two Ronchi patterns superimposed on the same glass plate. As the fringes of the two amplitude maps $I_{MA}(x,y)$ and $I_{MB}(x,y)$ will cross, the position of an optical centre can be more precisely determined at the crossing points. Preferably, the method of the invention may comprise the step of combining said two amplitude maps $I_{MA}(x,y)$ and $I_{MB}(x,y)$, for instance by addition or multiplication.

In an alternative embodiment, the method of the invention may comprise the steps of:
  capturing a moiré image of the pattern, either by aliasing or by superposition with an additional grating at a different distance in the optical axis with respect to the object;
  calculating a Fourier transform of said moiré image in a spatial frequency domain;
  selecting at least one first- or higher-order spectrum of said Fourier transform of the moiré image and shifting it in said frequency domain so as to substantially place it at a central frequency of said Fourier transform; and
  carrying out a reverse Fourier transform of said at least one shifted first- or higher-order spectrum of said Fourier transform of the moiré image so as to obtain a complex function $g_M(x,y) = I_M(x,y)e^{i\phi_M(x,y)}$ wherein $I_M(x,y)$ is an intensity and $\phi_M(x,y)$ a phase, and $I_M(x,y)$ is linked to the contrast level in the moiré image.

As in the case of the Fourier analysis of the abovementioned composite image, a map of the amplitude $I_M(x,y)$ of the output of applying this Fourier method to the moiré image will show fringes corresponding to the moiré areas of least or most contrast, one of which contains the optical centre of the object.

Particularly advantageously, said steps may be carried out with the grating in a plurality of different distances in the optical path with respect to the object. When the grating distance is varied, these fringes will vary, except for the fringe corresponding to the optical centre of the object. The optical centre can thus be located more easily and unambiguously. In particular, by adding the amplitude maps, the fringe containing the optical centre of the object will be amplified with respect to the others.

Also particularly advantageously, said pattern may comprise two or more crossed sets of parallel fringes. This will generate moiré images with intersecting fringes, the optical centre of the object being marked by one of these intersections.

In particular, said phase and amplitude object may be a refractive object, said initial image being an image of said pattern through said refractive object. The method of the invention can thus be used, for instance, for the optical inspection of lenses, such as ophthalmic lenses, including progressive lenses, contact lenses or other lenses with complex refraction characteristics, or for the optical inspection of plate glass, thin plastic foils or other refractive objects.

Alternatively, said phase and amplitude object may be a reflective object, said initial image being an image of said pattern reflected by the reflective object. The deflectometry method of the invention can thus also be used for the optical inspection of mirrors, of silicon wafers or of other reflective objects, e.g. parabolic or elliptic reflectors.

The invention also relates to a deflectometry system for the optical inspection of a phase and amplitude object, comprising a grating forming a contrast-based periodic pattern; an imaging system comprising an objective and an imaging sensor comprising a plurality of sensor elements; a data processing system connected to said imaging sensor; and means for holding said object in an optical path between said grating and the imaging system. The deflectometry system of the invention differs from that disclosed in abovementioned U.S. Pat. No. 6,496,253 B1 in that said data processing system is programmed to:

calculate a Fourier transform, in a spatial frequency domain, of a first image of said pattern distorted by said phase and amplitude object;

select a first-order spectrum of said Fourier transform and shifting it in said frequency domain towards a central frequency of said Fourier transform; and carry out a reverse Fourier transform of said shifted first-order spectrum of said Fourier transform so as to obtain a complex function $g(x,y)=I(x,y)e^{i\phi(x,y)}$, wherein $I(x,y)$ is an intensity and $\phi(x,y)$ a phase linked to optical deflection angles $\theta_x$, $\theta_y$ in, respectively, the directions of the x and y axes, according to the following formula:

$$\phi(x,y)=-2\pi h(\mu_0 \tan\theta_x + \nu_0 \tan\theta_y).$$

Advantageously, said objective may be a telecentric objective. This has the advantage of providing a constant magnification factor independently of the distance between object and imaging system.

Advantageously, if said phase and amplitude object is a reflective object, the deflectometry system may further comprise a beam splitter for reflecting said pattern towards the reflective object while transmitting its distorted reflection towards the imaging system. The grating can thus be offset from the optical axis of the imaging system, avoiding thus obstruction and interference.

Advantageously, said pattern may comprise at least one set of equally-spaced parallel fringes, preferably in the form of a Ronchi pattern. Such a pattern provides an unambiguous carrier frequency for the Fourier deflectometry method of the invention.

Advantageously, said spatial frequencies $\mu_0$, $\nu_0$ may be about half the respective Nyquist frequencies of the imaging system on said axes x, y.

In an undistorted image of the pattern, the spatial frequency of the signal sampled perpendicularly to the pattern fringes would be that of the pattern fringes, divided by the magnification factor of the objective. However, the object could be one that increases, at least locally, the spatial frequency of the distorted image, such as, for example, a diverging spherical lens. A grating pattern spatial frequency of about half the Nyquist frequency of the image sensor perpendicularly to the fringes, multiplied by the magnification factor of the objective, will ensure for most practical cases an accessible dynamic range in the distorted image of about ⅙ to ⅚ the Nyquist frequency, thus maintaining a safe margin below said cut-off Nyquist frequency, and safely avoiding aliasing.

Advantageously, said pattern may comprise two substantially perpendicular sets of equally-spaced parallel fringes. Such a pattern substantially facilitates locating the optical centre of the object using the abovementioned digital moiré image, as it will generate two sets of intersecting moiré fringes, the optical centre being located at one of the fringe intersections.

Advantageously, the grating may be formed by a contrast pattern printed on a glass plate. This provides a simple yet effective pattern for the abovementioned method. Preferably, said contrast pattern is a metal lithographic pattern, ensuring a high precision of the pattern and thus low signal noise.

Alternatively, said grating may be formed by an active matrix screen, such as, for example, an LCD screen. Such an active matrix screen will allow to alter the pattern without moving the grating, either to generate non-parallel patterns, or to virtually shift the grating in the optical path.

The present invention relates also to a data storage medium comprising a set of instructions for a data processing system to carry out a deflectometry method according to the invention; to a set of signals in magnetic, electromagnetic, electric and/or mechanical form, comprising a set of instructions for a data processing system to carry out a deflectometry method according to the invention; and/or to a process of transmitting, via magnetic, electromagnetic, electric and/or mechanical means, a set of instructions for a data processing device to carry out a deflectometry method according to the invention.

As "data storage medium" is understood any physical medium capable of containing data readable by a reading device for at least a certain period of time. Examples of such data storage media are magnetic tapes and discs, optical discs (read-only as well as recordable or re-writable), logical circuit memories, such as read-only memory chips, random-access memory chips and flash memory chips, and even more exotic data storage media, such as chemical, biochemical or mechanical memories.

Particular embodiments of the invention will now be described in an illustrative, but not restrictive form, with reference to the following figures.

Figure 4:
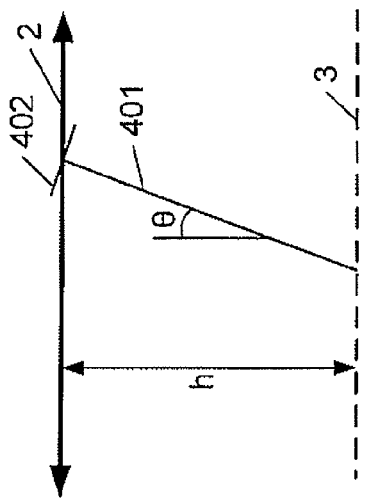
Figure 5:
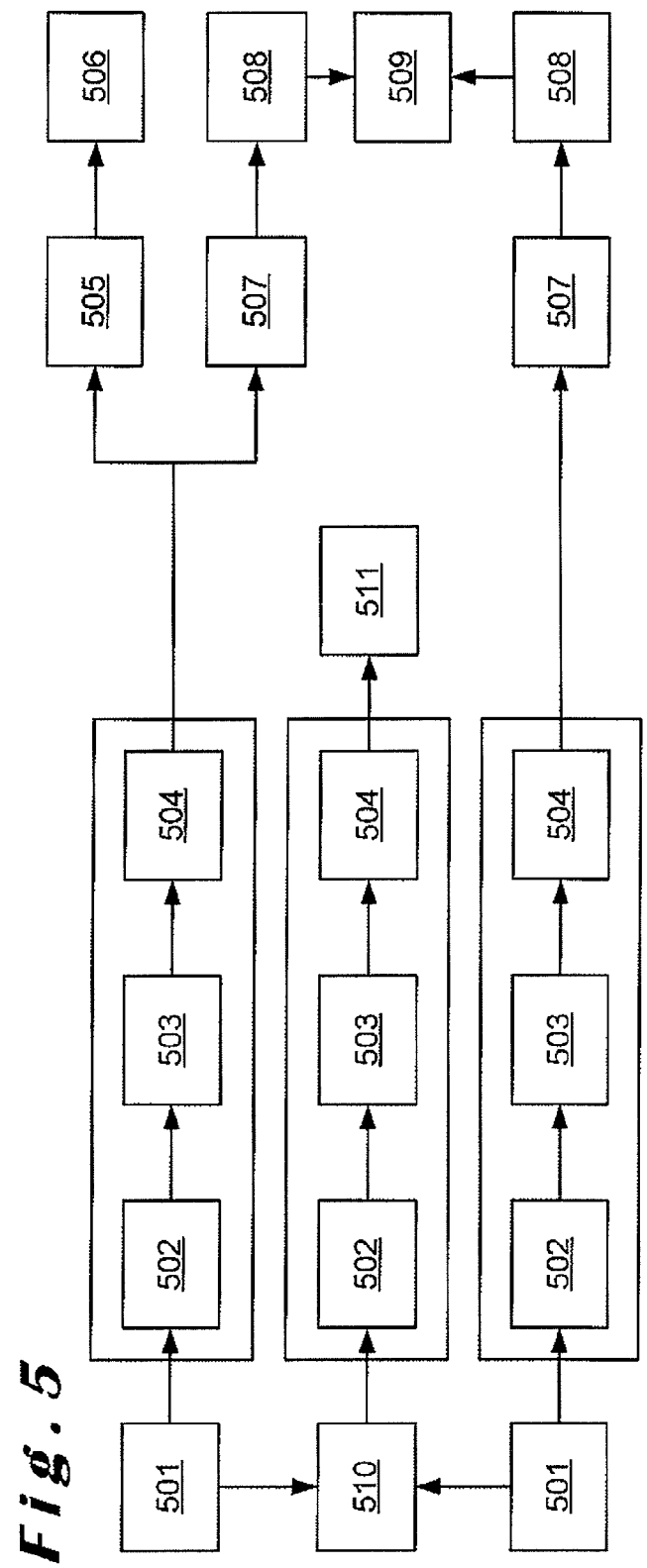
Figure 6:
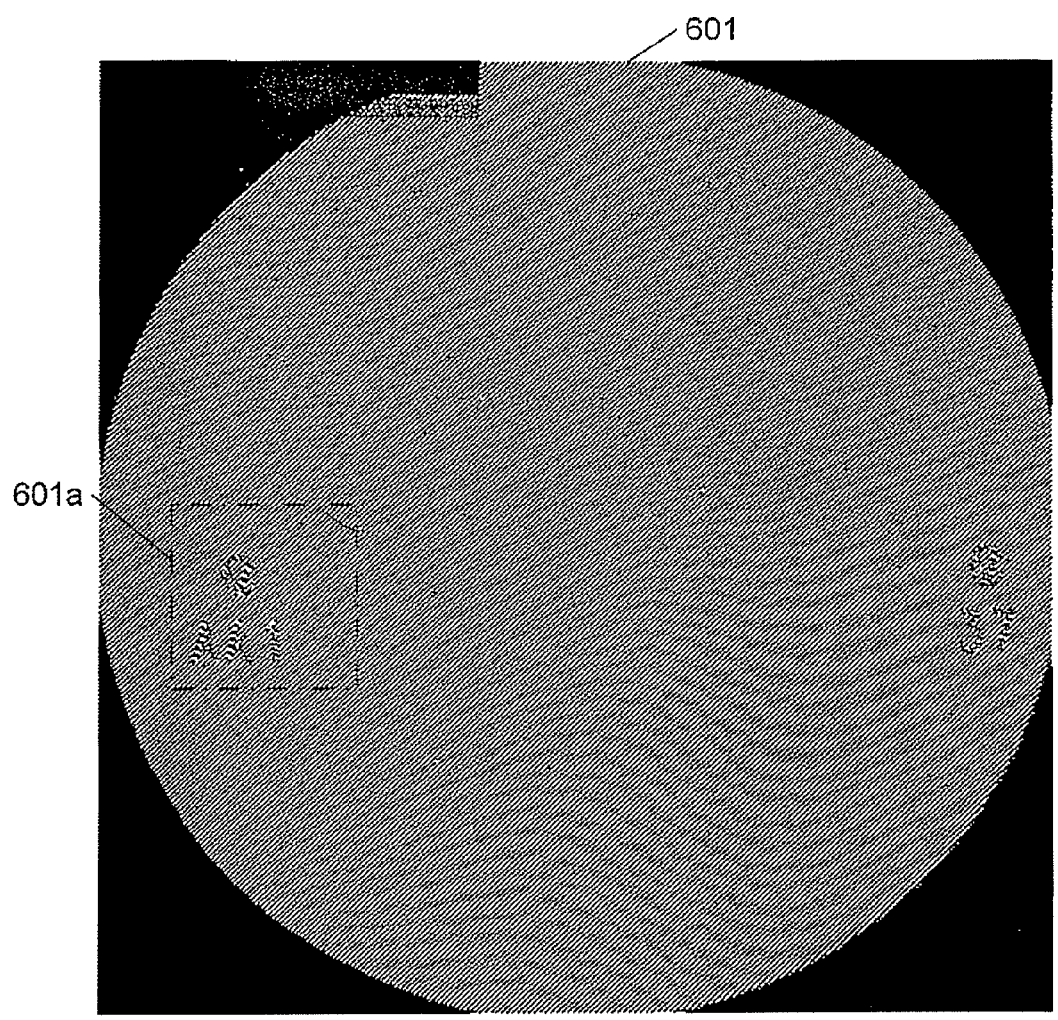
Figure 6A:
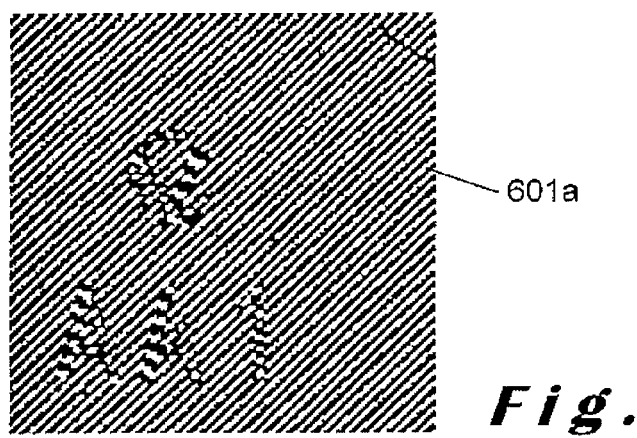
Figure 7:
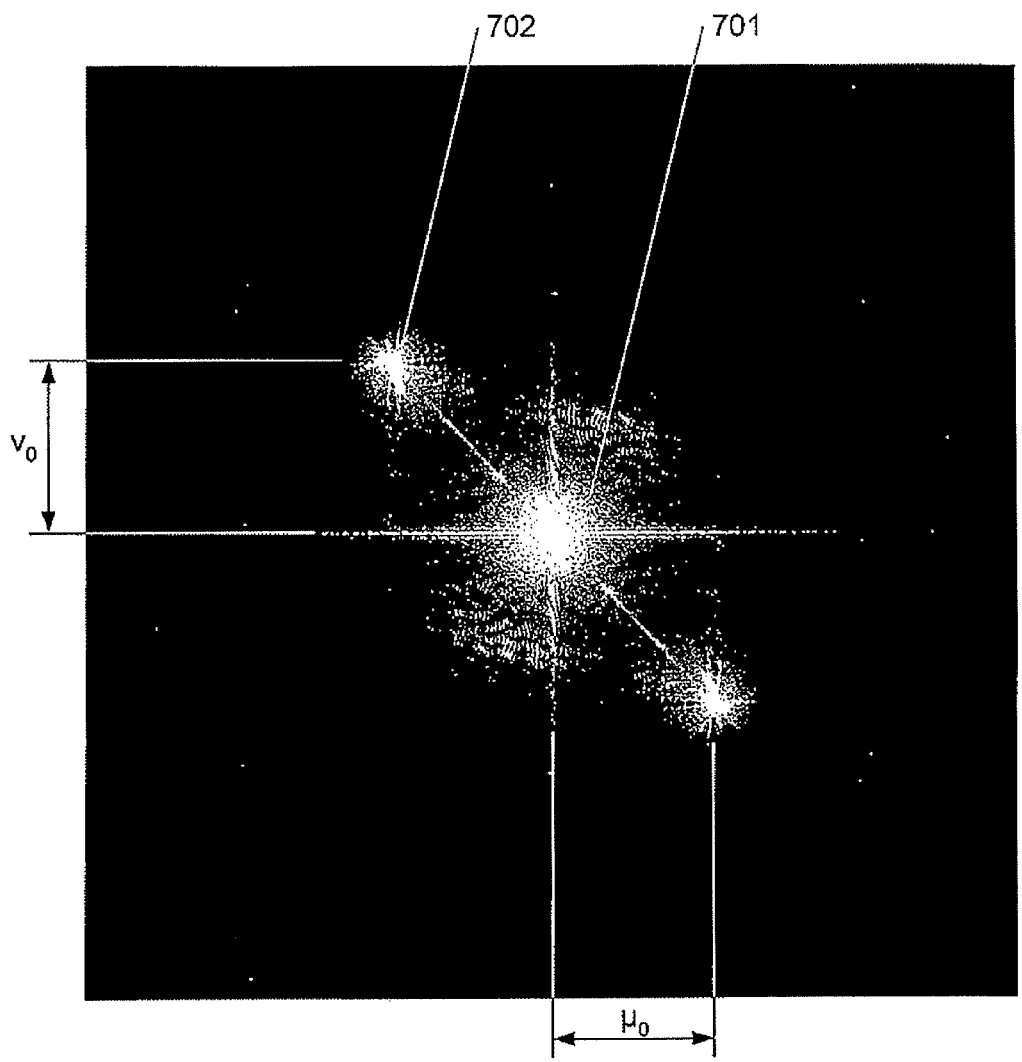
Figure 8:
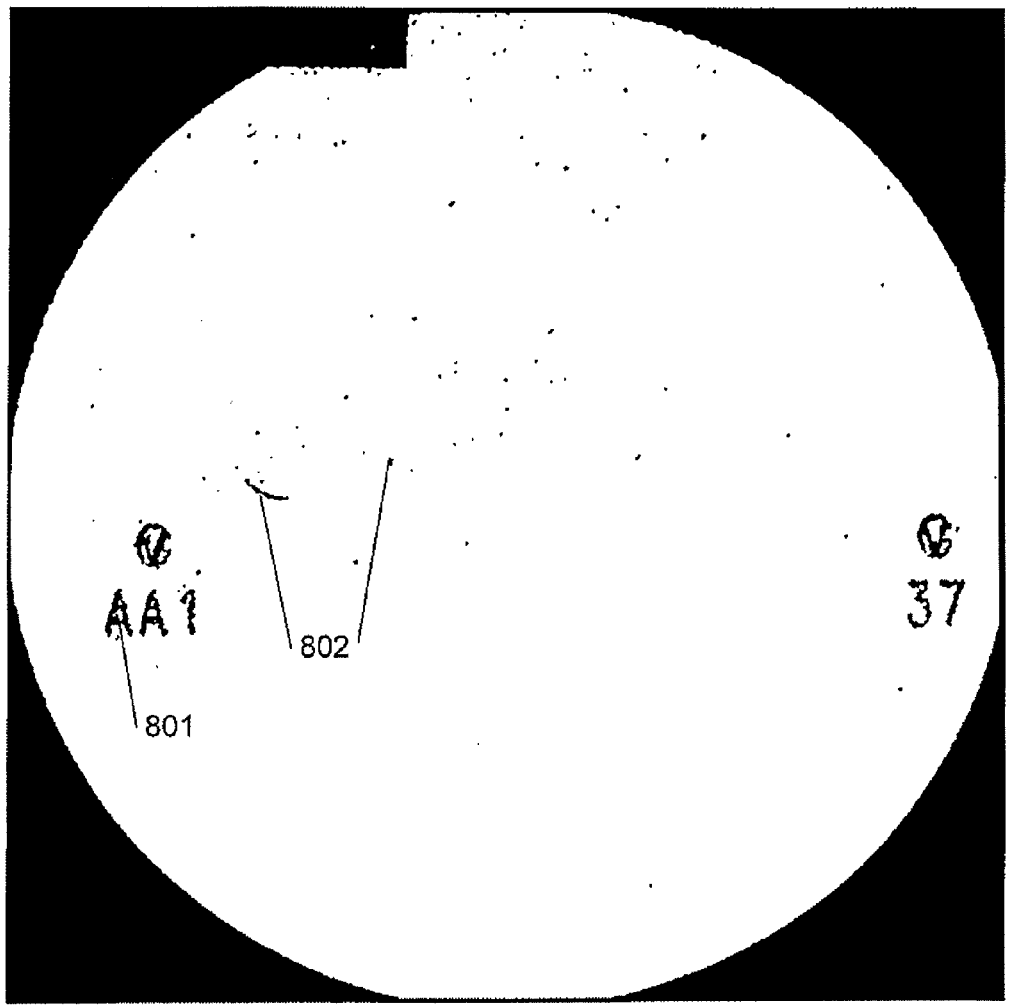
Figure 9:
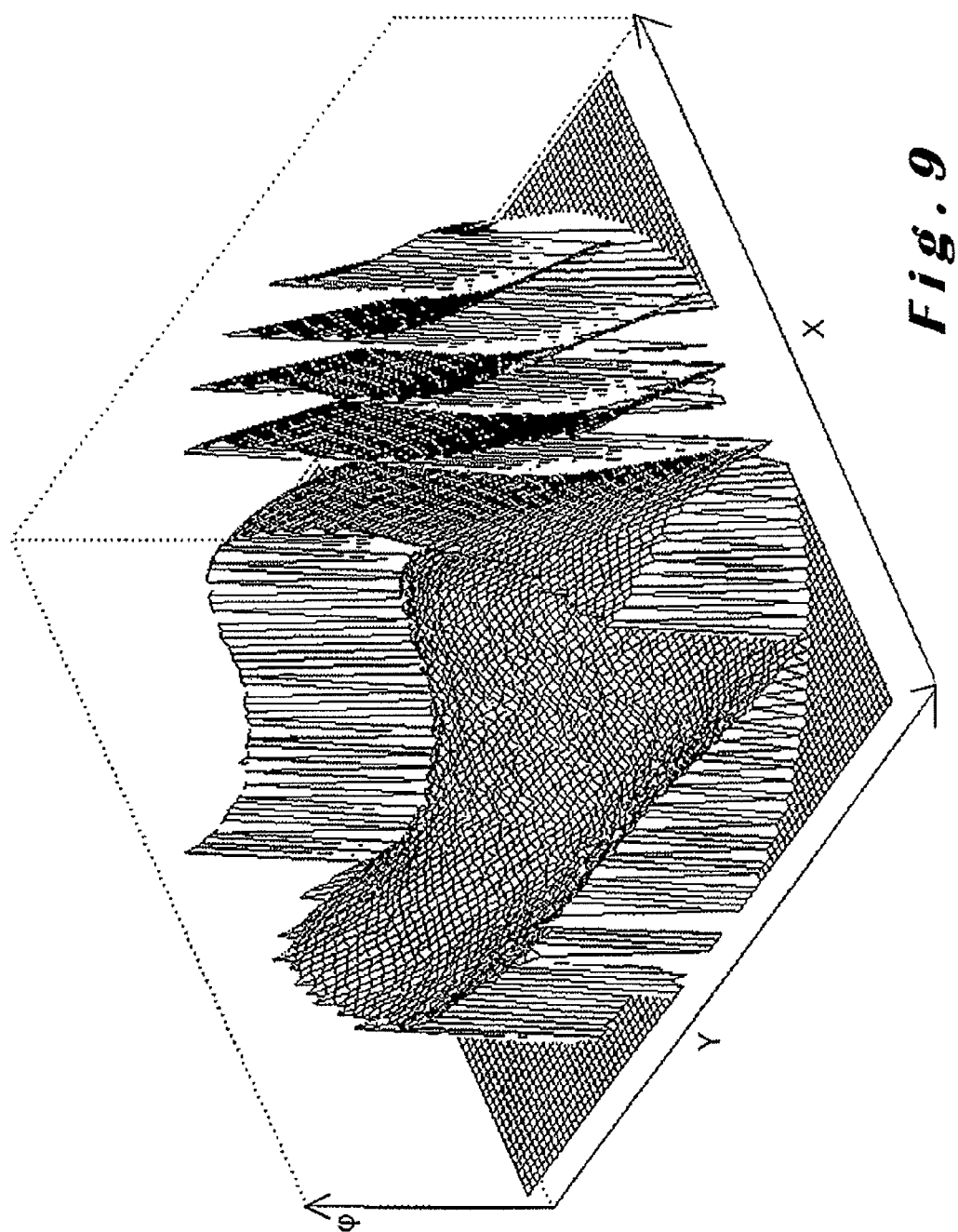
Figure 10:
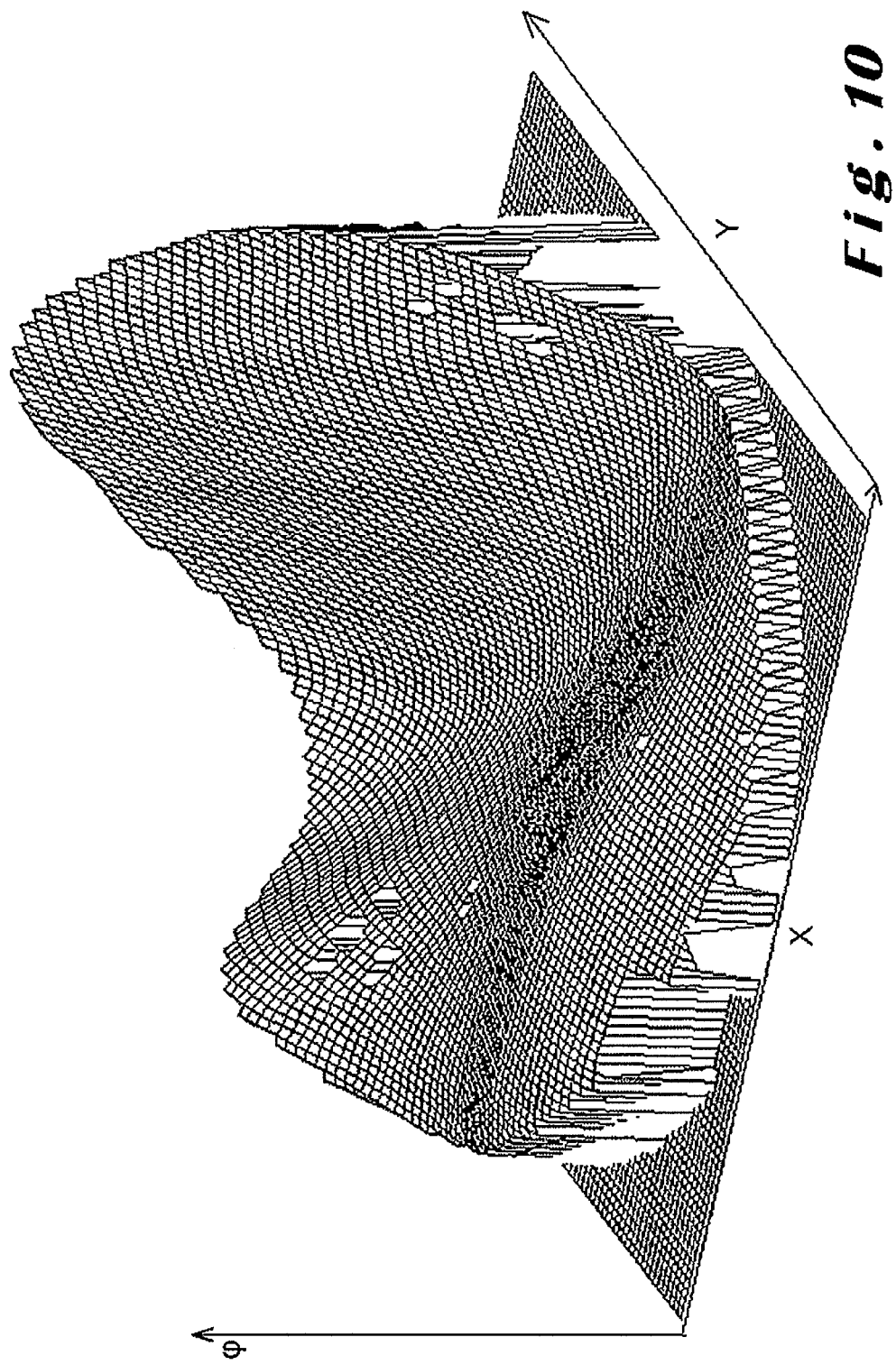
Figure 11:
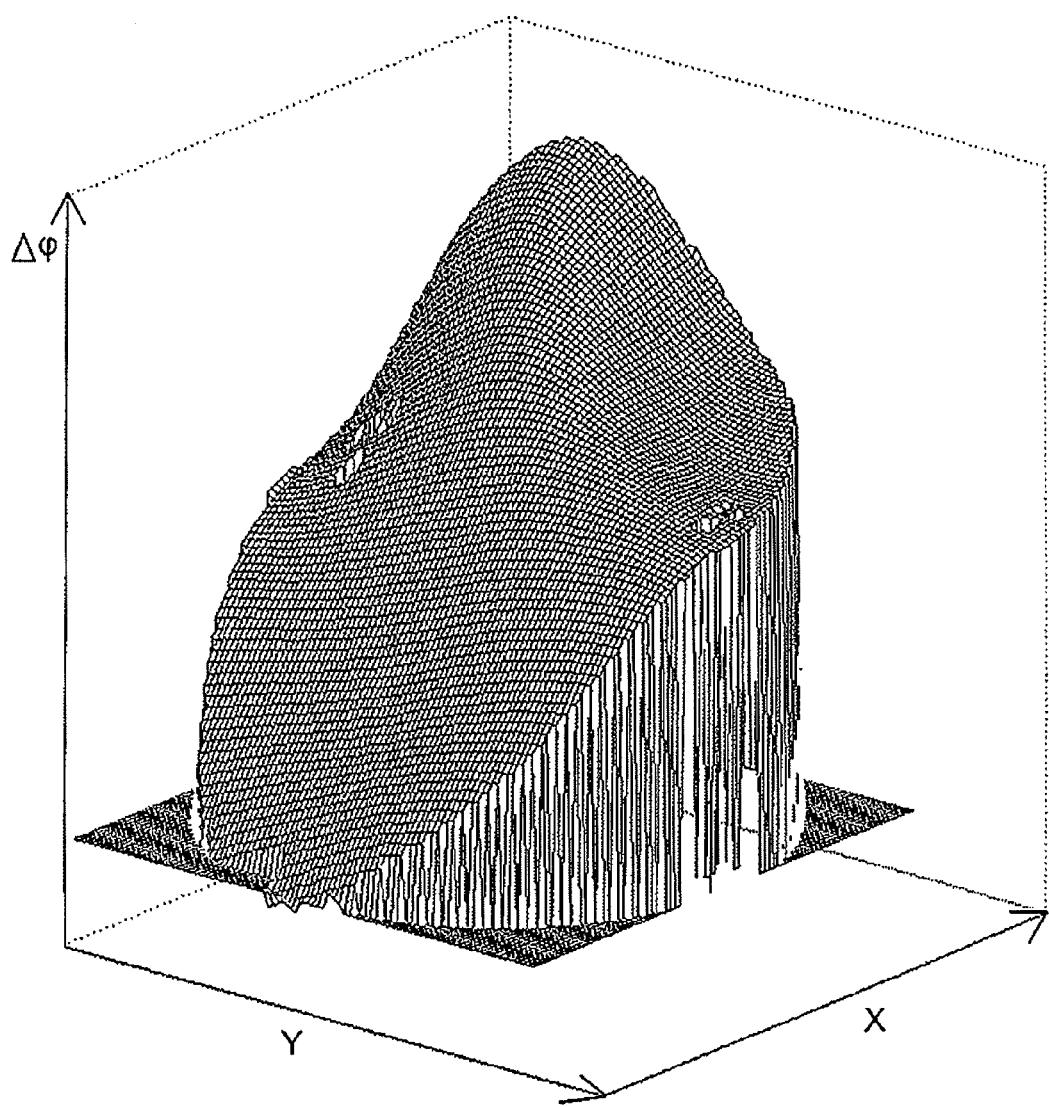
Figure 12:
Figure 13:
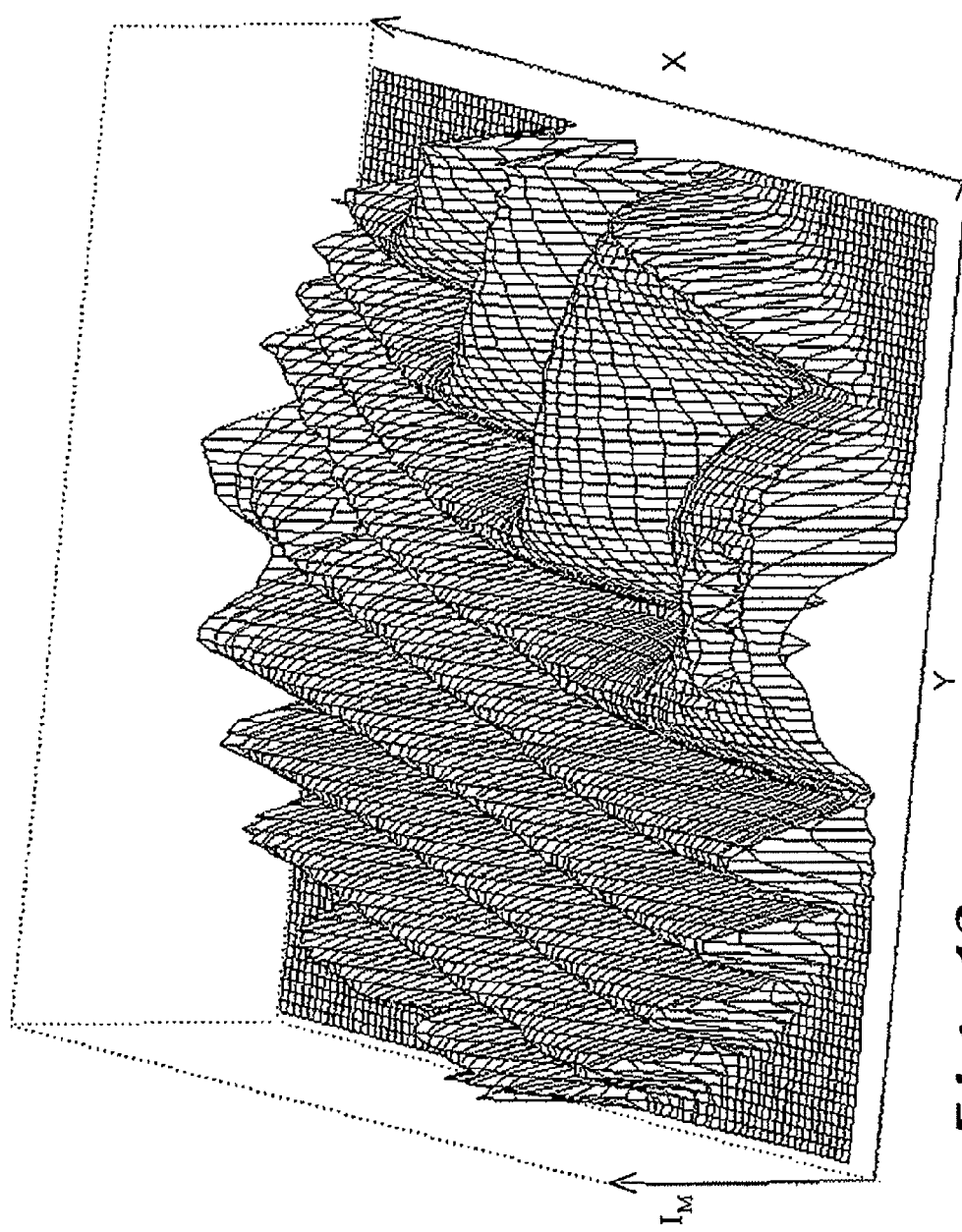
Figure 14:
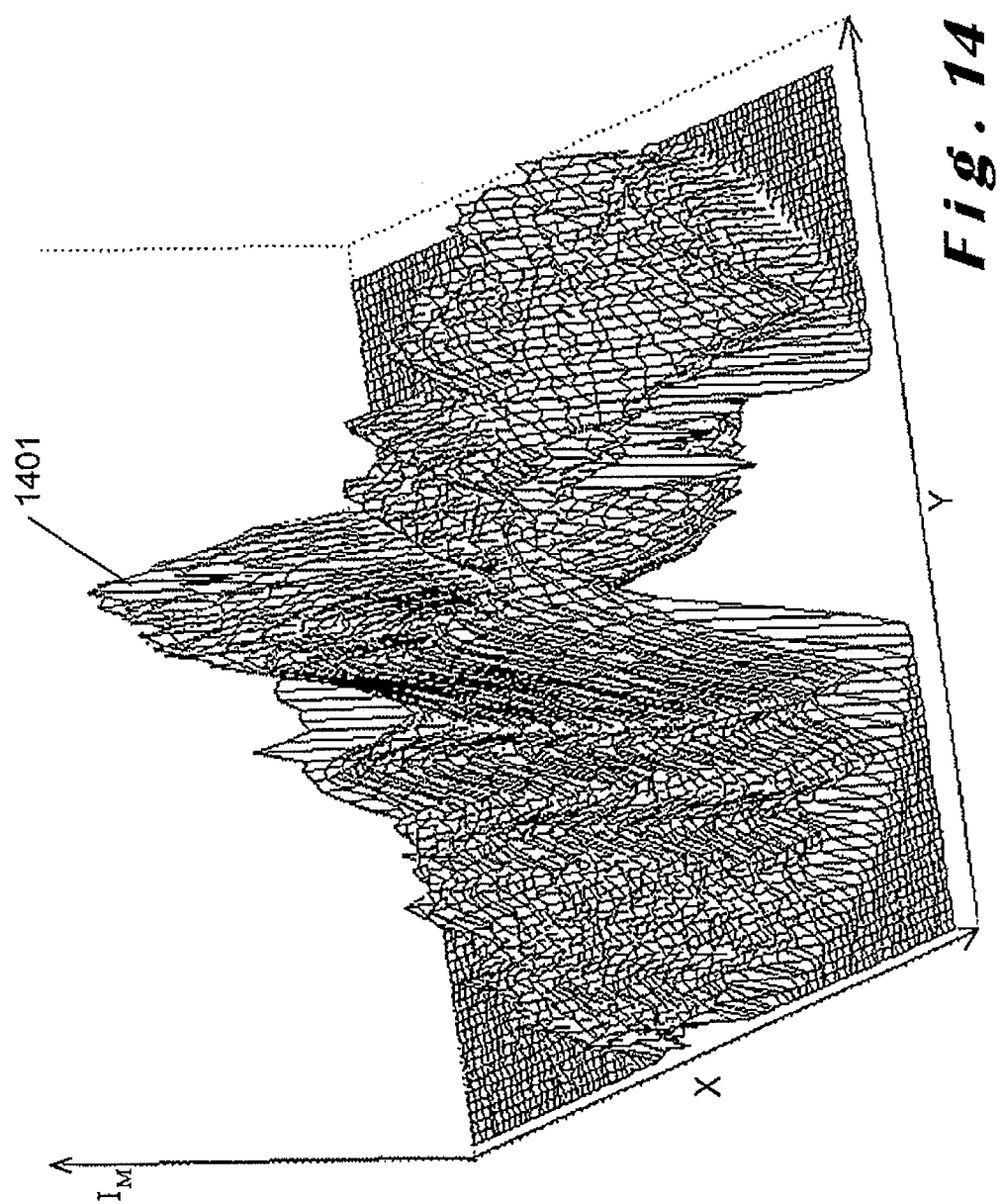

FIG. 4 schematically illustrates the relationship between wavefront, deflection angle and phase;

FIG. 5 shows a flowchart of an embodiment of a deflectometry method according to the invention;

FIG. 6 shows a contrast pattern image distorted by a phase and amplitude object in the optical path of said first embodiment;

FIG. 6a shows a detail of the image of FIG. 6;

FIG. 7 shows the Fourier transform of said distorted pattern in the spatial frequency domain;

FIG. 8 shows an enhanced-contrast amplitude map of the reverse Fourier transform of a shifted first-order spectrum of said Fourier transform;

FIG. 9 shows a phase map of the reverse Fourier transform of a shifted first-order spectrum of said Fourier transform;

FIG. 10 shows the same phase map after unwrapping;

FIG. 11 show the difference between two unwrapped phase maps as obtained from two different images acquired with the object at two different distances from the grating;

FIG. 12 shows a moiré composite image obtained by subtracting two images of the same pattern distorted by the phase and amplitude object at different relative positions of object and grating;

FIG. 13 shows an amplitude map of the reverse Fourier transform of a shifted first-order spectrum of the Fourier transform of said digital moiré image; and FIG. 14 shows an amplitude map of the reverse Fourier transform of a shifted first-order spectrum of the Fourier transform of a composite image obtained by combination of more than two images of the same pattern distorted by the phase and amplitude object at different relative positions of object and grating.

Figure 1:
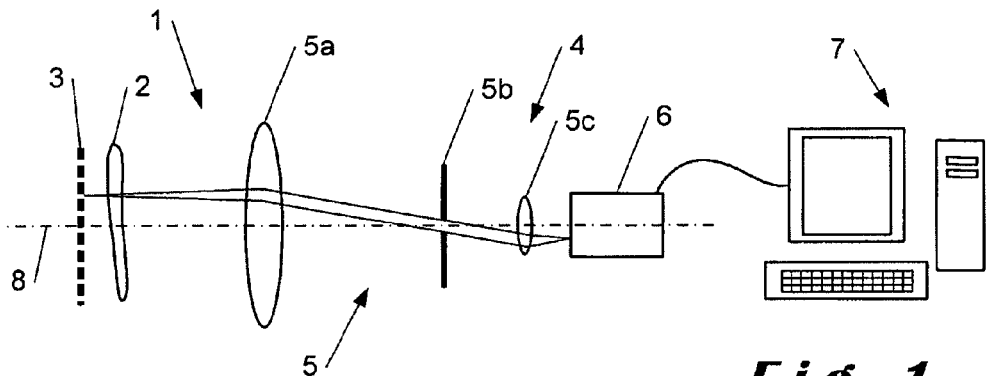
FIG. 1 shows a schematic view of a first embodiment of a deflectometry system according to the invention.

FIG. 1 shows a preferred embodiment of a deflectometry system 1 according to the invention for the optical inspection of a refractive object 2. This system comprises a grating 3 and an imaging system 4 comprising a telecentric objective 5 and an imaging sensor 6 connected to a data processing system 7. The telecentric objective 5 comprises a first set of optical elements 5a, an aperture 5b and possibly a second set of optical elements 5c. The imaging sensor 6 comprises a plurality of photosensitive elements, arranged in a square array in this particular embodiment. However, alternative arrangements of the photosensitive elements would also be considered by the skilled person, according to the circumstances. The grating 3 is in the optical axis 8 of the imaging system 4, so that the refractive object 2 can be placed between them in order to be optically inspected.

The grating 3 shows at least one contrast-based periodic pattern. For example, the grating 3 can be a Ronchi grating with a pattern formed by a set of parallel straight fringes, wherein the contrast follows a sinusoidal curve perpendicularly to the fringes. Two such sets of parallel fringes may also be arranged oriented in orthogonal directions, so as to form a square grid. In this preferred embodiment the grating 3 is formed by a glass plate on which the pattern has been printed, for instance using metal lithography. Alternatively, the grating could be formed by an active matrix screen, such as an LCD screen, or OLED display, which would allow to alter the pattern at will. This could permit, for instance, to virtually shift the grating 3 with respect to the object by altering the spatial frequency of the pattern.

Figure 2:
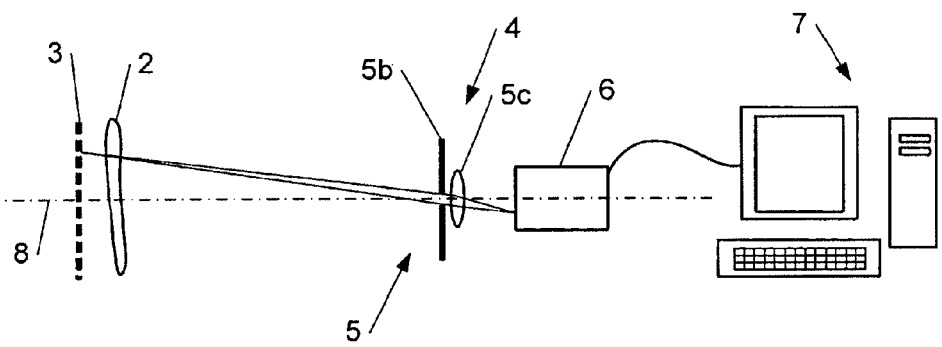
FIG. 2 shows a schematic view of a second embodiment of a deflectometry system according to the invention.

FIG. 2 shows a second, simplified embodiment of a deflectometry system 1 according to the invention. Like the embodiment illustrated in FIG. 1, this deflectometry system 1 comprises a grating 3, and an imaging system 4 comprising an objective 5 and an imaging sensor 6 connected to a data processing system 7. As in the preferred embodiment, the grating 3 is in the optical axis 8 of the imaging system 4, so that a refractive object 2 to be optically inspected can be inserted between them. The grating 3 is also of the same type as the grating 3 of the preferred embodiment. However, in this simplified embodiment, the objective 5 is not telecentric and comprises an aperture 5b and a set of optical elements 5c.

Figure 3:
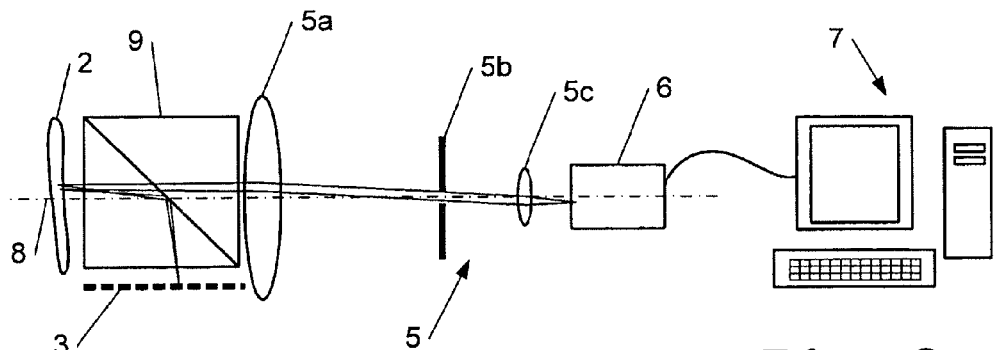
FIG. 3 shows a schematic view of a third embodiment of a deflectometry system according to the invention.

FIG. 3 shows a third embodiment of a deflectometry system 1 according to the invention, adapted to the optical characterisation of a reflective object 2. This embodiment also comprises a grating 3 and an imaging system 5. In this embodiment, to avoid obstructing the optical path, the grating 3 is offset from the optical axis 8 of the imaging system 5. To be nevertheless able to image a reflection of its pattern by the reflective object 2, the deflectometry system 1 further comprises a beamsplitter 9 placed in the optical axis 8 so as to reflect the image from the grating 3 towards the reflective object 2, while letting at least part of the light reflected by said reflective object 2 through towards the imaging system 4. In this way, the reflective object 2 can still be placed in an optical path between the grating 3 and the imaging system 4. As in the first embodiment, the imaging system 5 comprises a telecentric objective 5 and an imaging sensor 6. The telecentric objective 5 comprises a first set of optical elements 5a, an aperture 5b and second set of optical elements 5c. However, the skilled person would also contemplate alternative embodiments with a simplified imaging system as in the second embodiment. The grating 3 can also be of the same types as those of the first and second embodiments.

In order to inspect a refractive object in the first or second embodiments, or a reflective object in the third embodiment, according to the optical characterisation method of the invention, the object is inserted in the optical path between the grating 3 and the imaging system 5, as shown in FIGS. 1-3, so that it will distort the image of the grating 3 captured by the imaging sensor 6.

An embodiment of the deflectometry method of the invention will now be described with the optical inspection of an ophthalmic progressive correction lens using the deflectometry system 1 illustrated in FIG. 1 as an example.

In a first step 501 of this deflectometry method, as illustrated in FIG. 5, a distorted image 601 of a Ronchi grating 3 with a diagonal high spatial frequency pattern of parallel fringes 602, as seen through this phase and amplitude object 2 and the telecentric objective 5, is captured by the imaging sensor 6. Such a distorted image 601 is illustrated in FIG. 6. A detail 601a of this image 601 is illustrated in FIG. 6a, showing how the pattern is locally distorted by an identification microengraving of the object 2.

This image 601 can then be directly processed at the data processing system 7 in step 502 by performing a Fourier transform. Since this image 601 is captured by a 2D array of discrete photosensitive elements, this Fourier transform will be a 2D Discrete Fourier Transform (DFT). A particularly advantageous numerical method to do this is the Fast Fourier Transform (FFT) method. FIG. 7 illustrates this Fourier transform in logarithmic scale in the frequency domain. This Fourier transform shows a central peak 701, corresponding to its 0-order spectrum, and two first-order spectra 702, offset in the frequency domain, with respect to the central peak 701, by approximately the spatial frequencies $\mu_0$ and $v_0$ of the fringe pattern in, respectively, the x and y axes in the image plane.

In a next step 503, one of said first-order spectra 702 is selected and shifted towards the central frequency of the Fourier transform. This can be done, for example, by selecting, in said Fourier transform, a closed frequency region comprising said first-order spectrum 702, filtering out the rest of the Fourier transform and then performing a coordinate change so as to substantially place said first-order spectrum at the central frequency coordinates of the Fourier transform. Since the first-order spectra 702 will be offset by approximately $(\mu_0, v_0)$ from the central frequency coordinates of the Fourier transform, this can be performed by a coordinate change to the coordinates $(\mu', v')$, wherein $\mu' = \mu - \mu_0$ and $v' = v - v_0$. It must be noted that a different shift could be applied, but that this shift difference would have to be compensated afterwards by, for instance, a corresponding linear phase shift. This could be useful, for instance if the object 2 was a strong power lens, producing first-order spectra 702 offset from the central frequency coordinates by frequencies significantly different from $(\mu_0, v_0)$. It must also be noted, that, to improve the signal/noise ratio of this deflectometry method, it would also be possible to select not just one, but several, first- and/or higher-order spectra and shift all of them sequentially towards the central frequency coordinates. For each one of them, a phase map can be retrieved, and the several phase maps can be recombined.

In a step 504, a reverse Fourier transform is then performed on this shifted first-order spectrum 702, resulting in a complex array of points. Mapping the amplitude of this complex array in a step 505 results in an amplitude map revealing small features, such as dents, scratches or microengravings, locally affecting the transparency of the object 2. Since this method reveals features of a size of the same magnitude as the distance between fringes in the grating pattern, and in this method the spatial frequency of that pattern can be particularly high, it is thus possible to reveal particularly small features which would not be easily detected by other deflectometry methods. An additional step 506 can enhance the contrast by filtering out this amplitude below a certain threshold and setting all positions above that threshold at a maximum value. The result of such a contrast-enhancing step 506 is illustrated in FIG. 8. As can be seen in that figure, the microengraving 801 is clearly visible, as are small scratches, dents and marks 802 on the object 2. In combination with automatic character recognition of the microengraving 801, this can be used to automate the inspection process.

In parallel to the amplitude mapping step 505, a phase mapping step 507 can also be performed. This results in a wrapped phase map as shown in FIG. 9. This wrapped phase map can then be unwrapped by conventional means in step 508, resulting in the unwrapped phase map shown in FIG. 10.

This phase φ(x,y) is related to the angular deviation of the light rays 401 and the first-order derivative of the wavefront 402, as seen in abovementioned equations (7) and (8) and illustrated in FIG. 4. If the steps 501-504 and 507,508 are performed again with the grating 3 shifted to a different distance with respect to the object, it will result in a different phase map. Calculating in the next step 509 the phase differences Δφ between the maps results in a phase difference map as shown in FIG. 11. This phase difference at each point is proportional to the first-order derivative of the wavefront perpendicularly to the parallel fringes. The light deviation angle θ perpendicularly to the fringes can be retrieved in the next step 509 with the equation:

$$\theta(x, y) = \arctan\left(\frac{-p\Delta\varphi(x, y)}{2\pi\Delta h}\right) \qquad (14)$$

wherein p is the period of the pattern (that is, the inverse of the spatial frequency) at the grating 3, and Δφ and Δh the phase and distance differences, respectively. To retrieve the first-order derivatives in two different directions, the same steps can be repeated after rotating the pattern by a certain angle in the plane of the grating 3. The first order derivatives in the x and y directions can then be retrieved using abovementioned equations (12) and (13). The wavefront can also be reconstructed by numerical integration of those first-order derivatives.

If the distance h between the object 2 and the grating 3 is known, it will not be necessary to calculate the phase differences between two such phase maps obtained at different distances h between grating 3 and object 2. Instead, if a reference phase φ₀ is calculated by performing said Fourier method, that is, steps 502-504, on an undistorted image of the grating 3 with the object 2 removed from the optical path, the local light deviation angle can be calculated from the equation:

$$\theta(x, y) = \arctan\left(p\frac{(\varphi(x, y) - \varphi_0(x, y))}{2\pi h}\right) \qquad (15)$$

The numerical aperture NA of the telecentric objective 5 shall be adapted to the frequency of the pattern. It may be approximately 1.22λ/p, where λ is the wavelength. If the object 2 is brought out of focus by a distance h, the spatial uncertainty can be assessed as 2.44λ/ph, for a sufficiently large distance h.

The phase recovered as per this new method here is equivalent to the phase recovered by the Phase-shift Schlieren method, as disclosed, for example in US Patent Application US 2005/036153 A1. It can thus be processed in the same way to extract any parameters of interest, and a.o. the reconstruction of the wavefront, the calculation of refractive or reflective surface profiles.

The Fourier method, that is, steps 502-504, can also be applied to a composite image as illustrated in FIG. 12. Such a composite image may be created either by superposing two axially offset gratings 3 to obtain a moiré image, or by combining, digitally or otherwise, the distorted images of the same grating 3 at different distances from the object 2. The images may be combined in a step 510 by any suitable mathematical operation, such as, for example subtraction, addition or multiplication. Alternatively, a similar moiré image may be obtained by aliasing.

A subsequent step 511 of mapping of the amplitude $I_M(x,y)$ of the output of applying this Fourier method, with coordinate shifts in the Fourier domain equal or close to the carrier frequencies μ₀ and ν₀, to such a composite image in a step 511 will reveal areas of least or most contrast depending upon the mathematical operations that were performed to generate the composite image. If addition was used, step 511 will reveal the areas of most contrast, whereas if subtraction was used, step 511 will reveal the moiré areas of least contrast, for example. This is illustrated by the amplitude map shown in FIG. 13. If the grating distance h is varied, these moiré areas of least or most contrast will vary, except for an area comprising an optical centre of the object 2, that is, a point of the object 2 where there is no optical deflection. Since the displacement takes place along the optical axis, combining a plurality of such intensity maps will reveal a single low amplitude zone wherein the optical centre will be located.

If the distance h between the object 2 and the grating 3 can be changed arbitrarily, small steps can be applied first to roughly locate the optical centre, followed by larger displacements for refining the position of the optical centre.

It is also possible to unambiguously detect the optical centre by applying the abovementioned Fourier method to a combination (by e.g. addition, subtraction or multiplication) of more than two distorted images, for instance 15, captured with different distances h between grating 3 and object 2. The at least one optical centre then lies on a maximum 1401 of the resulting amplitude map, as shown on FIG. 14. Which maxima correspond to optical centres can be determined by thresholding.

In an preferred embodiment, a pattern is used presenting a periodic structure in two different directions, e.g. a square grid obtained by superposing two Ronchi patterns arranged orthogonally. It is then possible to carry out the abovementioned Fourier method first with a shift close to $\mu_{0,A}$, $\nu_{0,A}$, and then with a shift close to $\mu_{0,B}$, $\nu_{0,B}$ so as to obtain two amplitude maps, respectively $I_{MA}(x,y)$ and $I_{MB}(x,y)$ with crossing low amplitude fringes would be obtained, their intersections indicating potential effective optical centre. Preferredly, combining these amplitude maps $I_{MA}(x,y)$ and $I_{MB}(x,y)$, for instance by multiplication, and then thresholding the resulting composite map reveals the optical centre or centres.

Using the first embodiment of the deflectometry system of the invention, as illustrated in FIG. 1, it will be necessary to know the magnification factor in order to be able to integrate the wavefront derivatives and thereby calculate the wavefront. The magnification factor can be obtained directly by analysis of the image of the high spatial frequency pattern, which is assumed to be known precisely. The local non-linearities of the objective 5 can be corrected e.g. by analysis of the reference phase φ₀ as obtained by performing the Fourier method on an undistorted image of the pattern in absence of any phase and amplitude object 2 in the optical path between the grating 3 and the imaging system 4. The advantage of a telecentric objective 5 is that the magnification factor is independent of the distance between the object 2 and the objective 5, so that either the grating 3 or the object 2 may be moved in order to vary their relative distance h.

When using a deflectometry system as illustrated in FIG. 2 where the objective 5 is not telecentric, the same steps can be performed as described hereabove, but the distance from the object 2 to the aperture 5b will have to be known to evaluate the magnification factor. In this case, the detection of the optical centre becomes more complicated. The simplest option is by translating the grating 3 along the optical path, and to subtract to the distorted image, the reference image of the grating 3 in absence of the object 2, for the same position of the grating 3. However, this would only be practicable for thin lenses. Nevertheless, for what regards the cosmetic or micro-engravings inspection, this embodiment does not present any drawback.

It is also possible to recover the light deviation angle θ by changing the distance between the object 2 and the aperture 5b, while maintaining a constant distance h between the grating 3 and the object 2. In this embodiment of the deflectometry method of the invention, in order to keep the magnification factor constant, the aperture 5b may be translated along the optical axis 8 of the imaging system 4

A reflective object 2 may be inspected applying the same methods with, for instance, the deflectometry system 1 of FIG. 3.

Although the present invention has been described with reference to specific exemplary embodiments, it will be evident that various modifications and changes may be made to these embodiments without departing from the broader scope of the invention as set forth in the claims. Accordingly, the description and drawings are to be regarded in an illustrative sense rather than a restrictive sense.

The invention claimed is:

1. A deflectometry method for the optical inspection of a phase and amplitude object placed in an optical path between a single grating and an imaging system, at a distance h of the grating, wherein the grating forms a contrast-based periodic pattern with the spatial frequencies $\mu_0$, $v_0$ in, respectively, orthogonal axes x,y in an image plane, and the imaging system comprises an objective and an imaging sensor comprising a plurality of photosensitive elements, wherein this method comprises the step of:

capturing through the objective, with the imaging sensor, a first image of said pattern distorted by the phase and amplitude object;

and is characterised in that said spatial frequencies $\mu_0$, $v_0$ are not higher than the respective Nyquist frequencies of the imaging system on said axes x,y, and this method also comprises the steps of:

calculating a Fourier transform of said first image in a spatial frequency domain;

selecting at least one first— or higher-order spectrum of said Fourier transform and shifting it in said frequency domain so as to substantially place it at a central frequency of said Fourier transform; and carrying out a reverse Fourier transform of said at least one shifted first- or higher-order spectrum of said Fourier transform so as to obtain a complex function $g(x,y)=I(x,y)e^{i\phi(x,y)}$, wherein $I(x,y)$ is an intensity and $\phi(x,y)$ a phase linked to optical deflection angles $\theta_x$, $\theta_y$ in, respectively, the directions of the x and y axes, according to the following formula: $\phi(x,y)=-2\pi h(\mu_0 \tan\theta_x + V_0 \tan\theta y)$.

2. The deflectometry method according to claim 1, wherein several first- and/or higher order spectra of said Fourier transform are selected and shifted in said frequency domain so as to substantially place them at a central frequency of said Fourier transform.

3. The deflectometry method according to claim 1, further comprising a step of unwrapping said phase.

4. The delfectometry method according to claim 1, further comprising a step of filtering said intensity below a certain threshold.

5. The deflectometry method according to claim 1, wherein said steps are carried out with two patterns crossed at an angle with respect to each other.

6. The deflectometry method according to claim 1, wherein said steps are carried out with the grating in a first position with respect to the object and with the grating in a second position with respect to the object, said first and second positions being offset by a known distance along the optical path.

7. The deflectometry method according to claim 1, wherein several distorted images of the pattern are captured, with the object at several distances in said optical path with respect to the grating, and additionally comprising the steps of:

combining said several distorted images to obtain a composite image;

calculating a Fourier transform of said composite image in a spatial frequency domain;

selecting at least one first- or higher-order spectrum of said Fourier transform of the composite image and shifting it in said frequency domain so as to substantially place it at a central frequency of said Fourier transform; and carrying out a reverse Fourier transform of said at least one shifted first- or higher-order spectrum of said Fourier transform of the composite image so as to obtain a complex function $g_M(x, y)=I_M(x,y)e^{i\phi_M(x,y)}$ wherein $I_M(x,y)$ is an intensity and $\phi_M(x,y)$ a phase, and $I_M(x,y)$ is linked to the contrast level in the composite image.

8. The deflectometry method according to claim 7, wherein said pattern comprises two crossed sets of parallel fringes with different spatial frequencies $\mu_{O,A}$, $v_{O,A}$ and $\mu_{O,B}$ $v_{O,B}$ and said steps of calculating a Fourier transform of the composite image, selecting and shifting said spectrum of said Fourier transform of the composite image, and carrying out a reverse Fourier transform of said shifted spectrum of the Fourier transform of the composite image may be carried out first with a shift close to $\mu_{O,A}$, $V_{O,A}$, and then with a shift close to $\mu_{O,B}$, $V_{O,B}$ so as to obtain two amplitude maps, respectively $I_{MA}(x,y)$ and $I_{MB}(x,y)$.

9. The deflectometry method according to claim 8, further comprising a step of combining said two amplitude maps by superposition, addition, and/or multiplication.

10. The deflectometry method according to claim 1, further comprising the steps of:

capturing a moire image of the distorted pattern, either by aliasing or by superposition with an additional grating at a different distance in the optical axis with respect to the object;

calculating a Fourier transform of said moire image in a spatial frequency domain;

selecting at least one first- or higher-order spectrum of said Fourier transform of the moire image and shifting it in said frequency domain so as to substantially place it at a central frequency of said Fourier transform; and carrying out a reverse Fourier transform of said at least one shifted first— or higher-order spectrum of said Fourier transform of the moire image so as to obtain a complex function $g_M(x,y)=I_M(x,y)e^{i\ \Phi(x,y)}$ wherein $I_M(x,y)$ is an intensity and $\phi_m(x,y)$ a phase, and $I_M(x,y)$ is linked to the contrast level in the moiré image.

11. The deflectometry method according to claim 10, wherein said steps are carried out with the additional grating in a plurality of different distances in the optical path with respect to the object.

12. The deflectometry method according to claim 7, wherein said pattern comprises two crossed sets of parallel fringes.

13. The deflectometry method according to claim 1, wherein said phase and amplitude object is a refractive object, and said first image is an image of said pattern through said refractive object.

14. The deflectometry method according to claim 1, wherein said phase and amplitude object is a reflective object, and said first image is an image of said pattern reflected by the reflective object.

15. A deflectometry system for the optical inspection of a phase and amplitude object, comprising:
- a grating forming a contrast-based periodic pattern with the spatial frequencies $\mu_0$, $V_0$ in, respectively, orthogonal axes x,y in an image plane;
- an imaging system comprising an objective and an imaging sensor comprising a plurality of photosensitive elements;
- a data processing system connected to said imaging sensor; and
- means for holding said object in an optical path between said grating and the imaging system, at a distance h of said grating;
- this deflectometry system being characterised in that said spatial frequencies $\mu_0$, $v_0$ are not higher than the respective Nyquist frequencies of the imaging system on said axes x,y, and in that said data processing system is programmed to:
- capture through the objective, with the imaging sensor, a first image of said pattern distorted by the phase and amplitude object;
- calculate a Fourier transform, in a spatial frequency domain, of said first image of said pattern distorted by said phase and amplitude object;
- select at least one first- or higher-order spectrum of said Fourier transform and shifting it in said frequency domain towards a central frequency of said Fourier transform; and
- carry out a reverse Fourier transform of said shifted first-order spectrum of said Fourier transform so as to obtain a complex function $g(x,y)=I(x,y)e^{i\,\phi(x,y)}$, wherein $I(x,y)$ is an intensity and $\phi(x,y)$ a phase linked to optical deflection angles $\theta_x$, $\theta_y$ in, respectively, the directions of the x and y axes, according to the following formula: $\phi(x,y)=-2\pi h(\mu_0 \tan\theta x + v_0 \tan\theta y)$.

16. The deflectometry system according to claim 15, wherein said objective is a telecentric objective.

17. The deflectometry system according to claim 15, wherein said phase and amplitude object is a reflective object, the deflectometry system further comprising a beam splitter for reflecting said pattern towards the reflective object while transmitting its distorted reflection towards the imaging system.

18. The deflectometry system according to claim 15, wherein said pattern comprises at least one set of equally-spaced parallel fringes, preferably in the form of a Ronchi pattern.

19. The deflectometry system according to claim 15, wherein those equally-spaced parallel fringes said spatial frequencies $\mu_0,\mu_0$ are about ½ the respective Nyquist frequencies of said imaging system on said axes x, y.

20. The deflectometry system according to claim 15, wherein said pattern comprises two substantially perpendicular sets of equally-spaced parallel fringes.

21. The deflectometry system according to claim 15, wherein said grating is formed by a contrast pattern, preferably a metal lithographic pattern, printed on a glass plate.

22. The deflectometry system according to claim 15, wherein said grating is formed by an active matrix screen, such as, for example, an LCD screen.

* * * * *